United States Patent [19]

Naumann et al.

[11] Patent Number: 4,537,888
[45] Date of Patent: Aug. 27, 1985

[54] SUBSTITUTED BENZOXAZINE DERIVATIVES AND FUNGICIDAL USE

[75] Inventors: Klaus Naumann; Hans Scheinpflug, both of Leverkusen; Hans-Jürgen Rosslenbroich, Langenfeld; Volker Paul, Soest, all of Fed. Rep. of Germany

[73] Assignee: Bayer Aktiengesellschaft, Leverkusen, Fed. Rep. of Germany

[21] Appl. No.: 527,442

[22] Filed: Aug. 29, 1983

[30] Foreign Application Priority Data

Sep. 17, 1982 [DE] Fed. Rep. of Germany ....... 3234529

[51] Int. Cl.$^3$ ..................... A01N 43/90; C07D 498/04
[52] U.S. Cl. ..................... 514/228; 514/232; 514/237; 514/239; 544/101
[58] Field of Search ..................... 544/101; 424/248.52, 424/248.56, 248.57, 248.58

[56] References Cited

U.S. PATENT DOCUMENTS 4,133,954 1/1979 Sturm ................................. 544/101

OTHER PUBLICATIONS

Comptes Rendus, Des Seances, De L'Academie Des Sciences, C. R. Acad. Sc. Paris, t. 270 (Feb. 2, 1970)-Series C, pp. 498–501, Gauthier-Villars Editeur.

*Primary Examiner*—Richard L. Raymond
*Attorney, Agent, or Firm*—Sprung, Horn, Kramer & Woods

[57] ABSTRACT

Novel Substituted benzoxazine derivatives of the formula

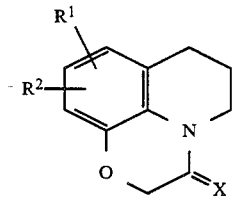

in which
 X is oxygen or suophur, and
 $R^1$ and $R^2$ each independently is hydrogen, alkyl, alkoxy, akylthio, halogenoalkyl, alkanoyl, aroyl, halogen, cyano, nitro, nitroso, amino or the suophonic acid grouping, with the restriction that either of $R^1$ and $R^2$ does not represent hydrogen if the other represents hydrogen, the 6-methyl group, the 6-ethyl group, the 6-butyl group or the 6-acetyl group and X is oxygen, which possess fungicidal activity. A few related compounds, though known, also possess such activity.

16 Claims, No Drawings

SUBSTITUTED BENZOXAZINE DERIVATIVES AND FUNGICIDAL USE

The invention relates to substituted benzoxazine derivatives, several processes for their preparation and their use as plant protection agents.

It is already known that certain substituted and unsubstituted benzoxazinones, such as, for example, 4,5-trimethylene-benzoxazin-3-one, 6-methyl- and 6-ethyl-4,5-trimethylene-1,4-benzoxazin-3-one, have fungicidal properties (compare U.S. Pat. No. 4,133,954). However, the action of these compounds is not always completely satisfactory, especially when low amounts and concentrations are applied. The preparation of other benzoxazinone derivatives, such as, for example, 6-butyl- or 6-acetyl-4,5-trimethylene-1,4-benzoxazin-3-one, is known (compare C.R. Acad. Sc. Paris, Ser. C. 1970, 270, 498–501). There is no information relating to an action in the area of plant protection.

New substituted benzoxazine derivatives of the general formula (I)

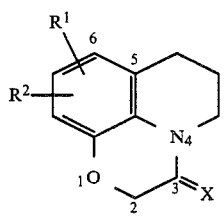

in which
X represents oxygen or sulphur and
$R^1$ and $R^2$ independently of one another represent hydrogen, alkyl, alkoxy, alkylthio, halogenoalkyl, alkanoyl, aroyl, halogen, cyano, nitro, nitroso, amino or the sulphonic acid grouping, with the restriction that either of $R^1$ and $R^2$ does not represent hydrogen if the other represents hydrogen, the 6-methyl group, the 6-ethyl group, the 6-butyl group or the 6-acetyl group and X represents oxygen,
have been found.

It has furthermore been found that the new substituted benzoxazine derivatives of the formula (I)

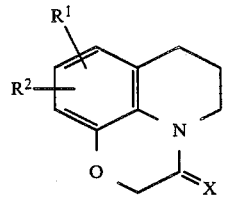

in which
X represents oxygen or sulphur and
$R^1$ and $R^2$ independently of one another represent hydrogen, alkyl, alkoxy, alkylthio, halogenalkyl, alkanoyl, aroyl, halogen, cyano, nitro, nitroso, amino or the sulphonic acid grouping, with the restriction that either of $R^1$ and $R^2$ does not represent hydrogen if the other represents hydrogen, the 6-methyl group, the 6-ethyl group, the 6-butyl group or the 6-acetyl group and X represents oxygen, are obtained by a process in which
(a) 4,5-trimethylenebenzoxazinone of the formula (II)

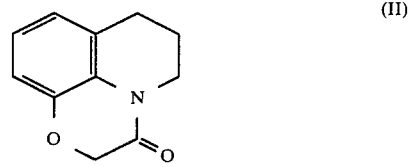

is substituted directly with suitable electrophilic reagents, such as, for example halogenating agents, nitrating agents or sulphonating agents, if appropriate in the presence of a catalyst and if appropriate in the presence of a diluent, or in which (b) 8-hydroxy-1,2,3,4-tetrahydroquinolines of the formula (III)

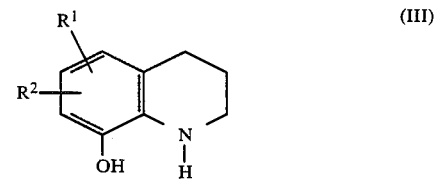

in which
$R^1$ and $R^2$ have the abovementioned meaning, are cyclized with a halogenoacetyl halide, if appropriate in the presence of an acid-binding agent and if appropriate in the presence of a diluent, or in which (c) the benzoxazinones according to the invention obtained by process (a) or (b), of the formula (Ia)

$R^1$ and $R^2$ have the abovementioned meaning, are converted into the corresponding benzoxazine-thiones of the formula (Ib)

in which
$R^1$ and $R^2$ have the abovementioned meaning, with phosphorus pentasulphide or other sulphurizing agents, if appropriate in the presence of a diluent, or in which (d) the nitrobenzoxazine derivatives according to the invention obtained according to process (a), (b) or (c), of the formula (Ic)

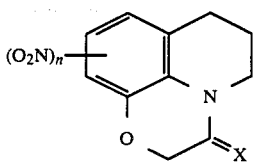

(Ic)

in which

X represents oxygen or sulphur and n represents 1 or 2, are reduced with hydrogen in the presence of a catalyst and in the presence of a diluent, if appropriate under pressure, to give the corresponding amino compounds of the formula (Id)

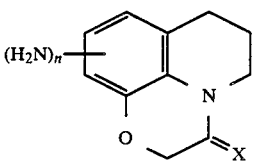

(Id)

in which n and X have the abovementioned meaning, or in which (e) the aminobenzoxazine derivatives according to the invention obtained according to process (d), of the abovementioned formula (Id), are diazotized with sodium nitrite and a mineral acid of the formula HA in the presence of a diluent, and the resulting diazonium salts of the formula (Ie)

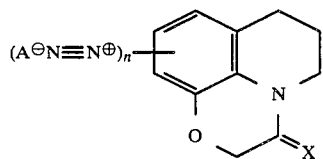

(Ie)

in which n and X have the abovementioned meaning and $A^{\ominus}$ represents the anion of a strong mineral acid, are substituted with suitable nucleophilic reagents in the presence of a diluent and if appropriate in the presence of a catalyst in the manner of a so-called Sandmeyer reaction, nitrogen being split off, or the so-called Balz-Schiemann variant, that is to say thermal decomposition of the corresponding diazonium tetrafluoroborate compound, is used to introduce a fluorine atom. The CN-group can be introduced by thermal decomposition of the corresponding dry diazonium tetracyanocuprates in an analogous way.

It has furthermore been found that the substituted benzoxazine derivatives of the formula (I), in which $R^1$, $R^2$ and X have the above-mentioned meaning plus derivatives wherein one of $R^1$ and $R^2$ represents hydrogen if the other represents a butyl group or an acetyl group in 6-position, have powerful fungicidal properties. Surprisingly the compounds exhibit a better fungicidal activity, especially when used systemically, than the benzoxazinones known from the prior art (compare U.S. Pat. No. 4,133,954). The substances according to the invention thus represent an enrichment of the art.

Formula (I) provides a general definition of the substituted benzoxazine derivatives according to the invention.

Preferred compounds of the formula (I) are those in which

X represents oxygen or sulphur and $R^1$ and $R^2$ independently of one another represent hydrogen, straight-chain or branched alkyl, alkoxy or alkylthio with up to 12 carbon atoms, halogenoalkyl with 1 to 4 carbon atoms and 1 to 5 halogen atoms, in particular fluorine, chlorine and bromine, alkylcarbonyl with up to 6 carbon atoms in the straight-chain or branched alkyl part, arylcarbonyl with 6 to 10 carbon atoms in the aryl part, fluorine, chlorine, bromine, iodine, cyano, nitro, nitroso, amino and/or the sulphonic acid group, with the restriction that either of $R^1$ and $R^2$ does not represent hydrogen if respectively $R^2$ represents hydrogen, the 6-methyl group, the 6-ethyl group the 6-butyl group or the 6-acetyl group and X represents oxygen.

Particularly preferred compounds of the formula (I) are those in which

X represents oxygen or sulphur and $R^1$ and $R^2$ independently of one another represent hydrogen, straight-chain or branched alkyl with 1 to 10 carbon atoms, alkoxy or alkylthio with in each case 1 to 5 carbon atoms, halogenoalkyl with 1 or 2 carbon atoms and 1 to 5 halogen atoms, alkylcarbonyl with 1 to 4 carbon atoms in the alkyl part, arylcarbonyl with 6 to 10 carbon atoms in the aryl part, fluorine, chlorine, bromine, iodine, cyano, nitro, nitroso, amino or the sulphonic acid radical with the restriction that R respectively R does not represent hydrogen if $R^1$ respectively $R^2$ represents hydrogen, the 6-methyl group, the 6-ethyl group, the 6-butyl group or the 6-acetyl group and X represents oxygen.

Very particularly preferred compounds of the formula (I) are those in which

X represents oxygen or sulphur and $R^1$ and $R^2$ independently of one another represent hydrogen, methyl, ethyl, n- or i-propyl, n-, i-, s- and t-butyl, n- or i-pentyl, n- or i-hexyl, n-octyl, n-decyl, methoxy, ethoxy, i-propoxy, methylthio, chloromethyl, acetyl, propionyl, benzoyl, fluorine, chlorine, bromine, iodine, cyano, nitro, nitroso, amino and/or the sulphonic acid group, with the restriction that either of $R^1$ and $R^2$ does not represent hydrogen if the other represents hydrogen, the 6-methyl group, the 6-ethyl group, the 6-butyl group or the 6-acetyl group and X represents oxygen.

The following compounds of the formula (I) may be mentioned specifically, in addition to the compounds mentioned in the preparation examples:

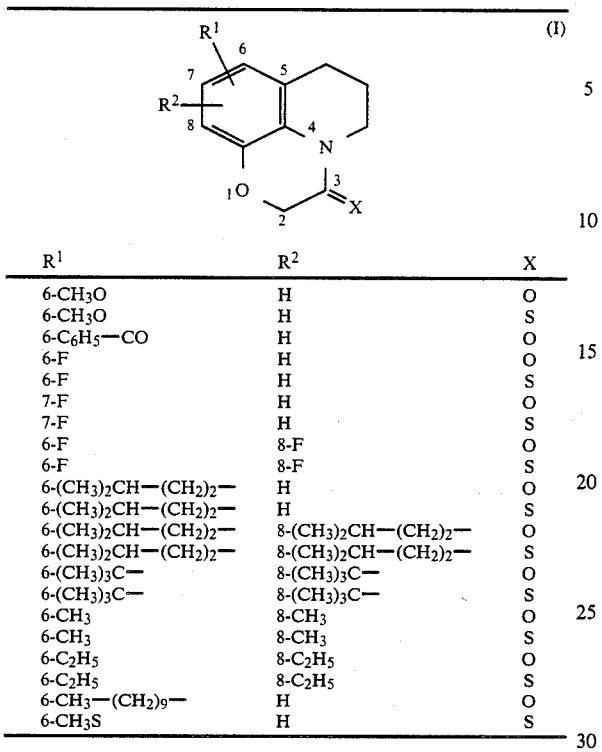

| R¹ | R² | X |
|---|---|---|
| 6-CH₃O | H | O |
| 6-CH₃O | H | S |
| 6-C₆H₅—CO | H | O |
| 6-F | H | O |
| 6-F | H | S |
| 7-F | H | O |
| 7-F | H | S |
| 6-F | 8-F | O |
| 6-F | 8-F | S |
| 6-(CH₃)₂CH—(CH₂)₂— | H | O |
| 6-(CH₃)₂CH—(CH₂)₂— | H | S |
| 6-(CH₃)₂CH—(CH₂)₂— | 8-(CH₃)₂CH—(CH₂)₂— | O |
| 6-(CH₃)₂CH—(CH₂)₂— | 8-(CH₃)₂CH—(CH₂)₂— | S |
| 6-(CH₃)₃C— | 8-(CH₃)₃C— | O |
| 6-(CH₃)₃C— | 8-(CH₃)₃C— | S |
| 6-CH₃ | 8-CH₃ | O |
| 6-CH₃ | 8-CH₃ | S |
| 6-C₂H₅ | 8-C₂H₅ | O |
| 6-C₂H₅ | 8-C₂H₅ | S |
| 6-CH₃—(CH₂)₉— | H | O |
| 6-CH₃S | H | S |

If, for example, 4,5-trimethylene-1,4-benzoxazin-3-one and chlorine are used as starting substances, the course of the reaction in process (a) according to the invention can be represented by the following equation:

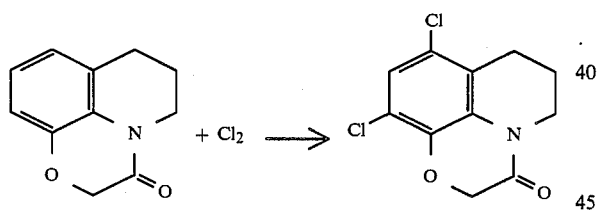

If, for example, 5-chloro-8-hydroxy-1,2,3,4-tetrahydroquinoline and chloroacetyl chloride are used as starting substances, the course of the reaction in process (b) according to the invention can be represented by the following equation:

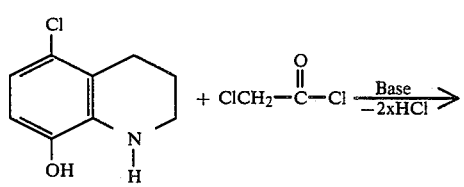

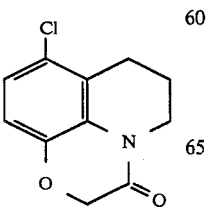

If, for example, 6-chloro-4,5-trimethylene-1,4-benzoxazin-3-one and phosphorus pentasulphide are used as starting substances, the course of the reaction in process (c) according to the invention can be represented by the following equation:

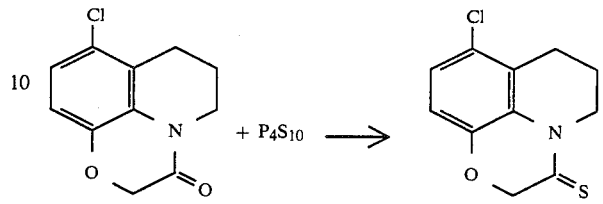

If, for example, 7-nitro-4,5-trimethylene-1,4-benzoxazin-3-one and hydrogen are used as starting substances, the course of the reaction in process (d) according to the invention can be represented by the following equation:

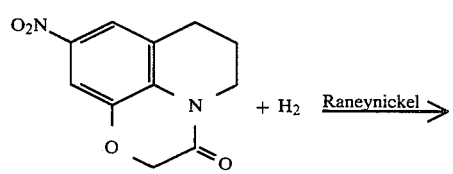

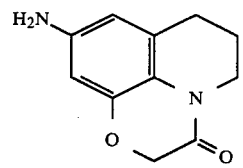

If, for example, 7-amino-4,5-trimethylene-1,4-benzoxazin-3-one and sodium nitrite/hydrochloric acid as well as copper cyanide are used as starting substances, the course of the reaction in process (e) according to the invention can be represented by the following equation:

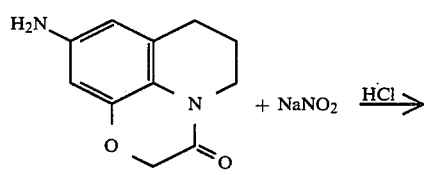

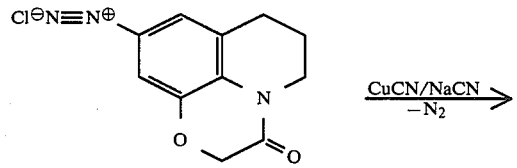

The 4,5-trimethylenebenzoxazin-3-one of the formula (II) required as a starting substance for process (a) according to the invention is known (compare U.S. Pat. No. 4,133,954).

The electrophilic reagents also required as starting substances for process (a) according to the invention are likewise known.

Reagents which are preferably used are halogenating agents, such as, for example, chlorine, bromine or interhalogen compounds, such as, for example, bromine chloride or iodine chloride, nitrating agents, such as nitric acid, nitrosating agents, such as nitrous acid, sulphonating agents, such as sulphuric acid, alkylating agents, such as, for example, alkyl chlorides or bromides or alcohols mixed with strong mineral acids, such as, for example, sulphuric acid, acylating agents, such as acyl chlorides or bromides, or chloromethylating agents, such as, for example, formaldehyde mixed with hydrogen chloride.

These are all generally known compounds.

Formula (III) provides a general definition of the 8-hydroxy-1,2,3,4-tetrahydroquinolines furthermore required as starting substances for process (b) according to the invention.

Hydroxy-1,2,3,4-tetrahydroquinolines of the formula (III) are generally known (compare, for example, Ind. J. Chem. 12 (1974), 252).

They are obtained, for example, by a process in which the corresponding substituted 8-hydroxyquinolines of the formula (IV)

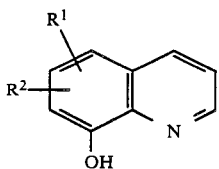
(IV)

in which $R^1$ and $R^2$ have the abovementioned meaning, are partially hydrogenated by known processes with hydrogen and a suitable hydrogenation catalyst, such as, for example, Raney nickel, in a diluent, such as, for example, tetrahydrofuran, at temperatures between 30° C. and 180° C., if necessary under pressure, or in which 8-hydroxy-1,2,3,4-tetrahydroquinoline of the formula (V)

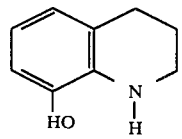
(V)

is substituted in the aromatic part with suitable electrophilic reagents in a known and customary manner, if appropriate in the presence of a diluent.

The substituted 8-hydroxyquinolines of the formula (IV) are known (compare, for example, J. Amer. Chem. Soc. 66, 1927 (1944)).

8-Hydroxy-1,2,3,4-tetrahydroquinoline of the formula (V) is likewise known (compare Chem. Ber. 14, 1368 (1881)).

The mineral acids of the formula HA furthermore required as starting substances for process (e) according to the invention are likewise generally known.

The mineral acids preferably used are hydrochloric acid, hydrobromic acid, sulphuric acid, nitric acid, perchloric acid and tetrafluoboric acid.

The nucleophiles furthermore required as starting substances for process (e) according to the invention are likewise generally known.

The nucleophiles which are preferably used are inorganic cyanides, such as, for example, sodium cyanide, potassium cyanide or copper cyanide, inorganic halides, such as, for example, sodium bromide, chloride or iodide as potassium bromide, chloride or iodide, or inorganic tetrafluoborates, such as, for example, ammonium tetrafluoborate.

Possible diluents for the reaction, according to the invention, in process (a) are organic or aqueous solvents.

These include, in particular, chlorinated hydrocarbons, such as, for example, carbon tetrachloride, chloroform and methylene chloride.

In individual cases, specific solvents are also suitable, thus, for example, in the case of the nitration and nitrosation reactions, in particular glacial acetic acid, or in the case of the alkylation and acylation reactions, in particular nitrobenzene.

Some of the reactions of process (a) according to the invention are preferably carried out in the presence of a suitable catalyst. In particular, copper nitrate or acetic anhydride is used for the nitration reactions. The nitrosation reaction can likewise be catalyzed by addition of acetic anhydride. Other possible catalysts for the nitrosation reactions are weak organic acids, such as, for example, acetic acid or p-toluene-sulphonic acid. Lewis acids, such as, for example, zinc dichloride, tin tetrachloride, boron trifluoride, aluminum trichloride or titanium tetrachloride, are preferably used as catalysts for the alkylation and acylation reactions.

The reaction temperatures can be varied within a wide range in process (a) according to the invention. The nitration, nitrosation and halogenation reactions are generally carried out between −80° C. and +80° C., preferably between −40° C. and +40° C. The sulphonation, alkylation and acylation reactions are generally carried out between −20° C. and +120° C., preferably between +20° C. and +100° C.

For carrying out process (a) according to the invention, 1 to 2 mols, preferably 1 to 1.5 mols, of nitrating, nitrosating, sulphonating, halogenating, alkylating or acylating agents are generally employed per mol of the benzoxazine compound of the formula (II).

Working up is in each case carried out in a known and customary manner.

Possible diluents for the reaction, according to the invention, in process (b) are inert organic solvents. These include, in particular, dipolar-aprotic solvents, such as, for example, acetonitrile or propionitrile, and furthermore amides, such as dimethylformamide, dimethylacetamide or N-methyl-formanilide, and in addition also dimethylsulphoxide, sulpholane and the highly polar hexamethylphosphoric acid triamide.

Process (b) according to the invention is carried out in the presence of acid-binding agents. All the inorganic and organic acid-binding agents which can customarily be used may be added. These include, preferably, alkali metal carbonates, such as, for example, sodium carbonate, potassium carbonate and sodium bicarbonate, and furthermore lower tertiary alkylamines, cycloalkylamines or arylalkylamines, such as, for example, triethylamine and N,N-dimethyl-benzylamine, and moreover pyridine as well as 1,4-diazabicyclo(2,2,2)-octane and 1,5-diazabicyclo(4,3,0)-non-5-ene.

The reaction temperature can be varied within a substantial range in carrying out process (b) according to the invention. In general, the reaction is carried out between 0° C. and 100° C., preferably between 10° C. and 80° C.

Process (b) according to the invention is generally carried out under normal pressure.

For carrying out process (b) according to the invention, 1.0 to 1.5 mols, preferably 1.0 to 1.2 mols, of chloroacetyl chloride are generally employed per mol of 8-hydroxy-1,2,3,4-tetrahydroquinoline of the formula (III).

The reaction is preferably carried out using one of the abovementioned acid-binding agents in one of the abovementioned diluents. The reaction mixture is stirred at the required temperature for several hours. Working up of the reaction mixture and isolation of the reaction products of the formula (I) according to the invention are carried out in a generally customary manner.

Possible diluents for the reaction, according to the invention, in process (c) are inert organic solvents. These include, preferably, chlorinated hydrocarbons, such as, for example, carbon tetrachloride, chlorobenzene and dichlorobenzene.

The reaction temperatures can be varied within a substantial range in carrying out process (c) according to the invention. In general, the reaction is carried out between +30° C. and +150° C., preferably at the boiling point of the solvent used.

Process (c) according to invention is generally carried out under normal pressure.

For carrying out process (c) according to the invention, 0.5 mol of phosphorus pentasulphide is preferably employed per mol of benzoxazine derivative of the formula (Ia). The reaction mixture is stirred at the required temperature for 10 minutes and the solid residue is then decanted and worked up in the customary manner.

Possible diluents for process (d) according to the invention are likewise inert organic solvents. These include, preferably, aliphatic or aromatic hydrocarbons, such as benzine, benzene, toluene or xylene; halogenated hydrocarbons, such as methylene chloride, chloroform, carbon tetrachloride or chlorobenzene; ethers, such as diethyl ether, dioxane or tetrahydrofuran; esters, such as ethyl acetate; and alcohols, such as methanol, ethanol or isopropanol.

All the customary hydrogenation catalysts can be used as catalysts for process (d), according to the invention. Raney catalysts, such as, for example, Raney nickel, or noble metal catalysts, such as, for example, platinum or palladium, if desired on a suitable support, such as, for example, charcoal, are preferably used.

The reaction temperatures can likewise be varied within a substantial range in carrying out process (d) according to the invention. In general, the reaction is carried out between +20° C. and +120° C., preferably between +60° C. and +100° C.

Process (d) according to the invention can be carried out under increased pressure. In general, it is carried out under between 1 and 100 bar, preferably between 1 and 80 bar.

In carrying out process (d) according to the invention, 0.5 to 5.0 g, preferably 1 to 3 g, of hydrogenation catalyst are added per 0.1 mol of nitrobenzoxazine derivative of the formula (Ic). The hydrogenation and working up and the isolation of the compounds of the formula (Id) are carried out by known and customary methods.

A possible diluent for process (e) according to the invention is, in particular, water.

If appropriate, process (e) according to the invention can be carried out in the presence of a suitable catalyst. Copper-I salts, such as, for example, copper-I cyanide, copper-I bromide or copper-I chloride, is preferably used.

The reaction temperatures can likewise be varied within a substantial range in carrying out process (e) according to the invention. In general, the reaction is carried out between +20° C. and +100° C., preferably between +40° C. and +100° C.

In carrying out process (e) according to the invention, 1 to 1.5 mols of sodium nitrite, preferably 1 to 1.2 mols of sodium nitrite, 2 to 5 mols of mineral acid, preferably 2 to 3 mols of mineral acid, and 1 to 5 mols of nucleophilic reagent, preferably 1 to 3 mols of nucleophilic reagent, are generally employed per mol of aminobenzoxazine derivative of the formula (Id).

The reaction is carried out and the mixture is worked up in a known and customary manner.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating rice diseases, such as, for example, against the causative organism Pyricularia oryzae.

It is also possible to combat Oomycetes and scab diseases, such as, for example, apple scab.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic material impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxider, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphonates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

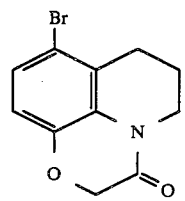

(Process a)

18.9 g (0.1 mol) of 4,5-trimethylene-1,4-benzoxazin-3-one are dissolved in 250 ml of carbon tetrachloride, and 7.1 g (0.1 mol) of bromine in 50 ml of carbon tetrachloride are added dropwise at 0° C., while stirring.

The reaction mixture is stirred at 60' C. until the evolution of HCl has ended (about 6 hours), and, after cooling, is filtered and concentrated in vacuo. The oil which remains crystallizes on trituration with ether. After filtration with suction and drying, 12 g (53% of theory) of 6-bromo-4,5-trimethylene-1,4-benzoxazin-3-one of melting point 133° C. are obtained.

EXAMPLE 2

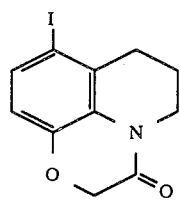

(Process a)

A solution of 18.6 g (0.1 mol) of iodine chloride in 10 ml of methylene chloride is added dropwise to a solution of 18.9 g (0.1 mol) of 4,5-trimethylene-1,4-benzoxazin-3-one in 250 ml of methylene chloride at −78° C.

When the addition has ended, the reaction mixture is allowed to come to room temperature, the solvent is removed in vacuo and the crystalline residue is washed with cold ethanol. After drying, 12.7 g (40% of theory) of 6-iodo-4,5-trimethylene-1,4-benzoxazin-3-one of melting point 191° C. are obtained.

EXAMPLE 3

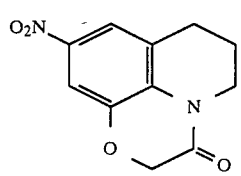

(Process a)

18.9 g (0.1 mol) of 4,5-trimethylene-1,4-benzoxazin-3-one are dissolved in a mixture of 200 ml of glacial acetic acid and 20 g (0.1 mol) of acetic anhydride, and 10 g (0.1 mol) of 66% strength nitric acid are added dropwise at 10° C., while stirring.

The reaction mixture is stirred at 20° C. to 25° C. for 2 hours, 100 ml of water are then added and the mixture is extracted several times with a total of 600 ml of methylene chloride. The combined organic extracts are dried over sodium sulphate and concentrated in vacuo. The brown oil which remains crystallizes into yellow crystals on trituration with ether. 19 g (80% of theory) of 7-nitro-4,5-trimethylene-1,4-benzoxazin-3-one of melting point 103° to 105° C. are obtained.

EXAMPLE 4

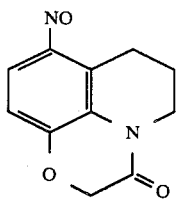

(Process a)

10 g (0.15 mol) of sodium nitrite are added in several portions to a solution of 18.9 g (0.1 mol) of 4,5-trimethylene-1,4-benzoxazin-3-one, 20 g (0.1 mol) of acetic anhydride and 17.2 g (0.1 mol) of p-toluenesulphonic acid in 200 ml of glacial acetic acid at 10° C., while stirring.

When the reaction has ended (about 2 hours), 200 ml of water are added and the mixture is extracted several times by shaking with methylene chloride. The combined organic extracts are dried over sodium sulphate and concentrated in vacuo. The product which remains can be recrystallized from cyclohexane. 8.7 g (40% of theory) of 6-nitroso-4,5-trimethylene-1,4-benzoxazin-3-one are obtained as a viscous oil.

$^1$H-NMR (δ in ppm): 7.7 (m, 2H), 4.75 (s, 2H); 3.95 (t, 2H); 2.95 (t, 2H); and 2.0 (quintet, 2H).

EXAMPLE 5

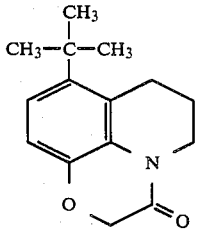

(Process a)

9.8 g (0.1 mol) of concentrated sulphuric acid are added dropwise to 18.9 g (0.1 mol) of 4,5-trimethylene-1,4-benzoxazin-3-one and 22.3 g (0.3 mol) of t-butanol at 80° C., while stirring.

When the addition has ended, the reaction mixture is boiled under reflux for 10 hours. For working up, the cooled reaction mixture is rendered alkaline with sodium hydroxide solution and is extracted several times with ether. The combined organic phases are dried over sodium sulphate and evaporated in vacuo. 22 g (90% of theory) 6-t-butyl-4,5-trimethylene-1,4-benzoxazin-3-one of melting point 77° C. are obtained.

EXAMPLE 6

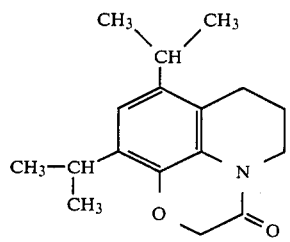

(Process a)

18.9 g (0.1 mol) of 4,5-trimethylene-1,4-benzoxazin-3-one and 33.3 g (0.25 mol) of aluminum trichloride are dissolved in 200 ml of nitrobenzene, and 40.5 g (0.3 mol) of isopropyl bromide are added dropwise at 10° C., while stirring.

The reaction mixture is poured onto ice and the organic phase is separated off, washed several times with water and dried over sodium sulphate. After the solvent has been distilled off in vacuo, the residue is recrystallized from cyclohexane. 12.3 g (45% of theory) of 6,8-diisopropyl-4,5-trimethylene-1,4-benzoxazin-3-one are obtained in the form of colorless crystals of melting point 71° C.

EXAMPLE 7

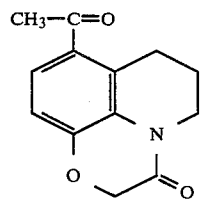

(Process a)

18.9 g (0.1 mol) of 4,5-trimethylene-1,4-benzoxazin-3-one and 33.3 g (0.25 mol) of aluminum trichloride are dissolved in 200 ml of nitrobenzene, and 7.9 g (0.1 mol) of acetyl chloride are added dropwise at 0° C.

For working up, the mixture is poured onto ice and extracted several times with methylene chloride. The combined organic extracts are washed with water, dried over sodium sulphate and concentrated in vacuo. 15 g (65% of theory) of 6-acetyl-4,5-trimethylene-1,4-benzoxazin-3-one are obtained in the form of colorless crystals of melting point 153° C. to 154° C.

EXAMPLE 8

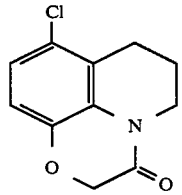

(Process b)

22 g (0.1 mol) of 5-chloro-8-hydroxy-1,2,3,4-tetrahydroquinoline hydrochloride, 11.3 g (0.1 mol) of chloroacetyl chloride and 41.4 g (0.3 mol) of potassium carbonate are boiled under reflux in 300 ml of acetonitrile for 5 hours.

The reaction mixture is allowed to cool and is filtered and the filtrate is concentrated in vacuo, whereupon the product crystallizes out. 19 g (85% of theory) of 6-chloro-4,5-trimethylene-1,4-benzoxazin-3-one of melting point 98° C. are obtained.

Preparation of the starting substance

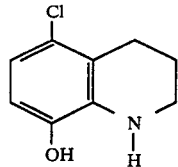
(III-1)

7.1 g (0.1 mol) of chlorine are passed into 14.9 g (0.1 mol) of 8-hydroxy-1,2,3,4-tetrahydroquinoline in 100 ml of methylene chloride at −78° C.

The mixture is allowed to come to room temperature and is stirred with active charcoal for 10 minutes and filtered and the filtrate is concentrated in vacuo. 16.5 g (75% of theory) of 5-chloro-8-hydroxy-1,2,3,4-tetrahydroquinoline are thus obtained.

14.5 g (55% of theory) of 5-bromo-8-hydroxy-1,2,3,4-tetrahydroquinoline (III-2) are obtained in an analogous manner using 11.5 g (0.1 mol) of bromine chloride instead of chlorine.

EXAMPLE 9

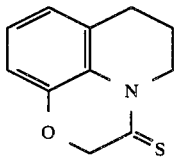
(Process c)

11.1 g (0.05 mol) of phosphorus pentasulphide are added in portions to 18.9 g (0.1 mol) of 4,5-trimethylene-1,4-benzoxazin-3-one in 200 ml of chlorobenzene, while stirring.

The mixture is heated at the reflux temperature for 10 minutes and is allowed to cool and the undissolved residue is decanted off. Concentration of the solvent gives 19.5 g (95% of theory) of 4,5-trimethylene-1,4-benzoxazine-3-thione of melting point 103° C.

EXAMPLE 10

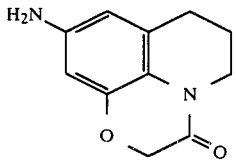
(Process d)

5.8 g (0.025 mol) of 7-nitro-4,5-trimethylene-1,4-benzoxazin-3-one are dissolved in 50 ml of tetrahydrofuran, 1 g of Raney nickel is added and the mixture is heated at 60° C. with hydrogen under pressure (80 bar) for 2 hours.

When the reaction has ended, the catalyst is filtered off and the solvent is evaporated in vacuo. The crystal sludge which remains is boiled up with 100 ml of ether and, after cooling, the product is filtered off with suction and dried. 3.3 g (64% of theory) of 7-amino-4,5-trimethylene-1,4-benzoxazin-3-one of melting point 170° C. are obtained.

EXAMPLE 11

(Process e)

6.9 g (0.1 mol) of sodium nitrite are added to 20.4 g (0.1 mol) of 7-amino-4,5-trimethylene-1,4-benzoxazin-3-one in 50 ml (0.3 mol) of 50% strength hydrobromic acid.

The reaction solution is added dropwise to a solution of 14.3 g (0.1 mol) of copper-I bromide and 10.3 g (0.1 mol) of sodium bromide in 50 ml of water at 0° C. The mixture is warmed until the evolution of gas has ended. After cooling, the mixture is extracted several times with methylene chloride, the combined organic extracts are dried over sodium sulphate, the solvent is removed in vacuo and the solid thus obtained is recrystallized from cyclohexane. 13.4 g (50% of theory) of 7-bromo-4,5-trimethylene-1,4-benzoxazin-3-one are obtained in the form of yellow crystals of melting point 168° C.

The following compounds of the general formula (I) are obtained in a corresponding manner:

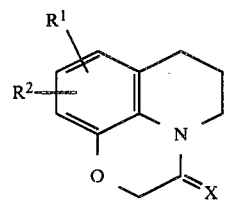
(I)

| Example No. | Structure | Physical properties |
|---|---|---|
| 12 | Cl, Cl substituted | Melting point 152° C.–156° C. |
| 13 | NC substituted | IR: 2.200 cm⁻ (CN band) Melting point 147°–149° C. |
| 14 | Cl substituted, thione | Melting point 104° C. |

-continued

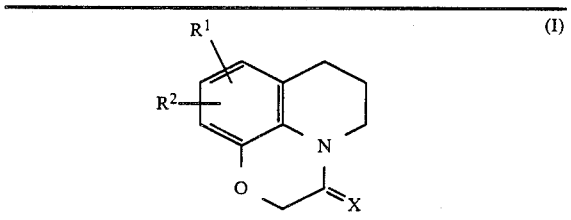

| Example No. | | Physical properties |
|---|---|---|
| 15 | 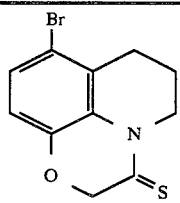 Br | Melting point 132° C. |
| 16 | 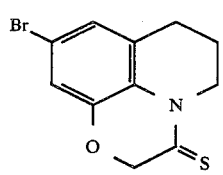 Br | Melting point 169° C.–172° C. |
| 17 | 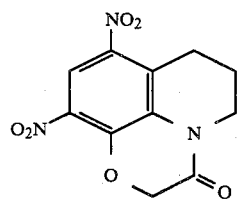 NO₂, O₂N | Melting point 142° C.–146° C. |
| 18 | 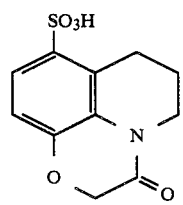 SO₃H | Melting point >280° C. |
| 19 | 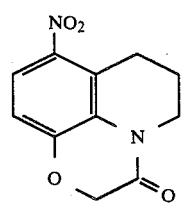 NO₂ | Melting point 162° C.–168° C. |
| 20 | 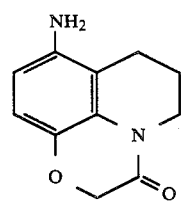 NH₂ | ¹H—NMR (δ in ppm): 6.7 (d, 1H); 6.3 (d, 1H); 4.65 (s, 2H); 3.85 (t, 2H); 3.4 (s, 2H); 2.55 (t, 2H); and 2.0 (quintet, 2H) |
| 21 | 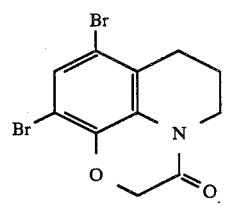 Br, Br | Melting point 193° C.–194° C. |

-continued

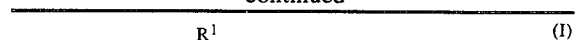

| Example No. | | Physical properties |
|---|---|---|
| 22 | 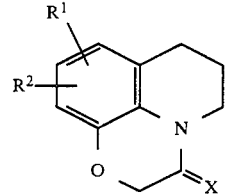 CN | Melting point 191° C.–193° C. |
| 23 | 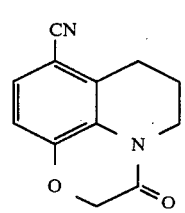 F | Melting point 90° C.–110° C. |
| 24 | 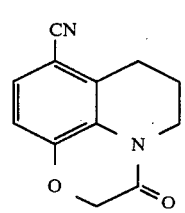 O₂N | Melting point 169° C.–173° C. |
| 25 | 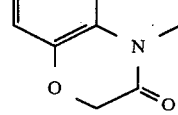 Br, Br | Oil |
| 26 | 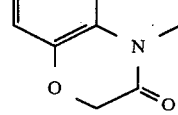 (CH₂)₁₁—CH₃, CH₃—(CH₂)₁₁ | Oil |

USE EXAMPLES

The substance shown here is used as a comparison example in the use examples which follow:

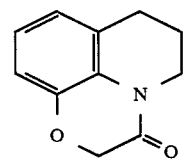 (A)

4,5-trimethylene-1,4-benzoxazin-3-one

EXAMPLE A

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 1, 3 and 8.

EXAMPLE B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a good activity is shown, for example, by the compounds according to the following preparation examples: 1, 3 and 8.

It will be understood that the specification and examples are illustrative but not limitative of the present invention and that other embodiments within the spirit and scope of the invention will suggest themselves to those skilled in the art.

What is claimed is:

1. A substituted benzoxazine derivative of the formula

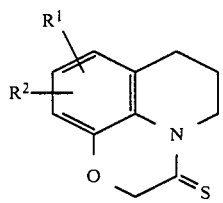

in which $R^1$ and $R^2$ each independently is hydrogen, alkyl, alkoxy, alkylthio, halogenoalkyl, alkanoyl, aroyl, halogen, cyano, nitro, nitroso, amino or the sulphonic acid grouping.

2. A compound selected from the group consisting of
5-bromo-4,5-trimethylene-1,4-benzoxazin-3-one,
6-chloro-4,5-trimethylene-1,4-benzoxazin-3-one,
6-iodo-4,5-trimethylene-1,4-benzoxazin-3-one, and
7-cyano-4,5-trimethylene-1,4-benzoxazin-3-one.

3. A substituted benzoxazine derivative according to claim 1,
in which
$R^1$ and $R^2$ each independently is hydrogen, alkyl, alkoxy or alkylthio with up to 12 carbon atoms, halogenoalkyl with 1 to 4 carbon atoms and 1 to 5 halogen atoms, alkylcarbonyl with up to 6 carbon atoms in the alkyl part, arylcarbonyl with 6 to 10 carbon atoms in the aryl part, fluorine, chlorine, bromine, iodine, cyano, nitro, nitroso, amino or the sulphonic acid grouping.

4. A substituted benzoxazine derivative according to claim 1, in which
$R^1$ and $R^2$ each independently is hydrogen, alkyl with 1 to 10 carbon atoms, alkoxy or alkylthio with in each case 1 to 5 carbon atoms, halogenoalkyl with 1 or 2 carbon atoms and 1 to 5 halogen atoms, alkylcarbonyl with 1 to 4 carbon atoms in the alkyl part, arylcarbonyl with 6 to 10 carbon atoms in the aryl part, fluorine, chlorine, bromine, iodine, cyano, nitro, nitroso, amino or the sulphonic acid grouping.

5. A substituted benzoxazine derivative according to claim 1, in which
$R^1$ and $R^2$ each independently is hydrogen, methyl, ethyl, n- or i-propyl, n-, i-, s- and t-butyl, n- or i-pentyl, n- or i-hexyl, n-octyl, n-decyl, methoxy, ethoxy, i-propoxy, benzoyl, fluorine, chlorine, bromine, iodine, cyano, nitro, nitroso, amino or the sulphonic acid grouping.

6. A compound according to claim 1, wherein such compound is 4,5-trimethylene-1,4-benzoxazine-3-thione of the formula

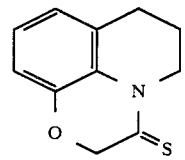

7. A compound according to claim 1, wherein such compound is 6-bromo-4,5-trimethylene-1,4-benzoxazine-3-thione of the formula

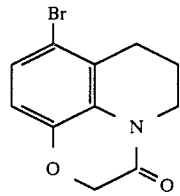

8. A compound according to claim 2, wherein such compound is 5-bromo-4,5-trimethylene-1,4-benzoxazin-3-one of the formula 9. A compound according to claim 2, wherein such compound is 6-chloro-4,5-trimethylene-1,4-benzoxazin-3-one of the formula

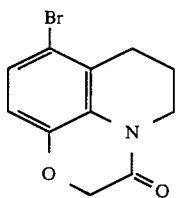

10. A compound according to claim 2, wherein such compound is 6-iodo-4,5-trimethylene-1,4-benzoxazin-3-one of the formula

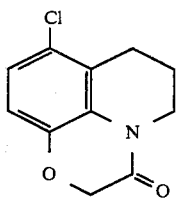

11. A compound according to claim 2, wherein such compound is 7-cyano-4,5-trimethylene-1,4-benzoxazin-3-one of the formula

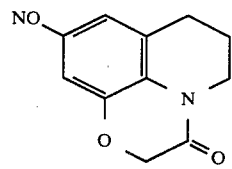

12. A fungicidal composition comprising a fungicidally effective amount of a compound according to claim 1 in admixture with a diluent.

13. A fungicidal composition comprising a fungicidally effective amount of a compound according to claim 2 in admixture with a diluent.

14. A method of combatting fungi which comprises administering to such fungi or to a fungus habitat a fungicidally effective amount of a compound according to claim 1.

15. The method according to claim 14, wherein such compound is 4,5-trimethylene-1,4-benzoxazine-3-thione or 6-bromo-4,5-trimethylene-1,4-benzoxazine-3-thione.

16. A method of combatting fungi which comprises administering to such fungi or to a fungus habitat a fungicidally effective amount of a compound according to claim 2.

* * * * *

UNITED STATES PATENT AND TRADEMARK OFFICE
CERTIFICATE OF CORRECTION

PATENT NO. : 4,537,888
DATED : August 27, 1985
INVENTOR(S) : Klaus Naumann, et al.

It is certified that error appears in the above-identified patent and that said Letters Patent is hereby corrected as shown below:

| | |
|---|---|
| Col. 11, line 10 | Delete "dimethylsulphoxider" and substitute --dimethylsulphoxide-- |
| Col. 11, line 30 | Delete "sulphonates", second instance and substitute --sulphates-- |
| Col. 20, line 67 | Before "bromo-" delete "5-" and substitute -- 6- -- |
| Col. 22, line 15 | Beginning of formula delete "NO\" and substitute --NC\-- |

Signed and Sealed this

Tenth Day of December 1985

[SEAL]

Attest:

DONALD J. QUIGG

Attesting Officer     Commissioner of Patents and Trademarks